US008165899B2

(12) United States Patent
Yeh et al.

(10) Patent No.: US 8,165,899 B2
(45) Date of Patent: Apr. 24, 2012

(54) SYSTEM AND METHOD FOR MANAGING FORM-GENERATED DATA

(75) Inventors: Chih-heng Thomas Yeh, Diamond Bar, CA (US); Lionel P. Ng, Pasadena, CA (US)

(73) Assignee: Medrule Business Solutions, Inc., Orange, CA (US)

( * ) Notice: Subject to any disclaimer, the term of this patent is extended or adjusted under 35 U.S.C. 154(b) by 1114 days.

(21) Appl. No.: 11/604,460

(22) Filed: Nov. 27, 2006

(65) Prior Publication Data
US 2007/0174087 A1 Jul. 26, 2007

Related U.S. Application Data

(60) Provisional application No. 60/758,842, filed on Jan. 13, 2006, provisional application No. 60/810,248, filed on Jun. 2, 2006.

(51) Int. Cl.
*G06F 19/00* (2011.01)
(52) U.S. Cl. ............... 705/3; 705/2; 715/222; 715/224; 600/300
(58) Field of Classification Search ............... 715/224; 705/2, 3; 345/179; 235/494
See application file for complete search history.

(56) References Cited

U.S. PATENT DOCUMENTS

| | | | | |
|---|---|---|---|---|
| 6,603,464 B1 * | 8/2003 | Rabin | | 345/179 |
| 7,134,606 B2 * | 11/2006 | Chou | | 235/494 |
| 2002/0050982 A1 | 5/2002 | Ericson | | |
| 2002/0107885 A1 * | 8/2002 | Brooks et al. | | 707/505 |
| 2002/0123909 A1 * | 9/2002 | Salisbury | | 705/3 |
| 2003/0046256 A1 | 3/2003 | Hugosson et al. | | |
| 2003/0167185 A1 * | 9/2003 | Gordon et al. | | 705/2 |
| 2003/0200119 A1 * | 10/2003 | Lewis et al. | | 705/2 |
| 2004/0254816 A1 * | 12/2004 | Myers | | 705/2 |
| 2005/0013104 A1 | 1/2005 | Feague et al. | | |
| 2005/0156909 A1 | 7/2005 | Lapstun et al. | | |
| 2005/0209903 A1 | 9/2005 | Hunter et al. | | |
| 2005/0256745 A1 * | 11/2005 | Dalton | | 705/3 |
| 2005/0262429 A1 | 11/2005 | Elder et al. | | |
| 2006/0007189 A1 | 1/2006 | Gaines, III et al. | | |
| 2006/0047539 A1 | 3/2006 | Huang | | |
| 2006/0085222 A1 | 4/2006 | Huang et al. | | |
| 2006/0259322 A1 * | 11/2006 | Chin et al. | | 705/2 |

OTHER PUBLICATIONS

Dialog search results, Dec. 17, 2011.*

* cited by examiner

*Primary Examiner* — Dilek B Cobanoglu

(57) ABSTRACT

A system and method for managing form-generated data related to a patient encounter involves translating location information related to a user writing on a form into a contextualized data element that includes contextual information. The contextual information helps to explain and/or give meaning to the user writing. Contextual information may include a descriptive name, an identification of data type, healthcare classification information, taxonomic information, an indication of the patient, an indication of the person that wrote on the form, and/or an indication of the date and time at which the writing occurred. The contextual information is then used by an Electronic Medical Record (EMR)/Electronic Health Record (EHR) application to perform a function such as patient/insurance billing, case management, or order fulfillment.

28 Claims, 10 Drawing Sheets

☐ Begin

| 1 | 2 |
| 3 | 4 |

| 1 | 2 |
| 3 | 4 |

| 1 | 2 |
| 3 | 4 |

| 1 | 2 |
| 3 | 4 |

Patient Name: _____

Chief Complaint: _____
_____
_____

Medical History: _____
_____

Diagnosis: 1 _____
2 _____
3 _____

Treatment: 1 _____
2 _____
3 _____

LAB Tests:     ⌐150
☐ Test A, 788.1
☐ Test B, 790.2
☐ Test C, 790.45

☐ Finalize

| Mapping Data Set | | |
|---|---|---|
| user-area = defined | label = pin*pad@1*1#7 |
| user-area = defined | label = pin*pad@1*2#7 |
| ⋮ | ⋮ |
| user-area = defined | label = pin*pad@4*4#7 |
| user-area = defined | label = chart*patient-name#2 |
| user-area = defined | label = chart*chief-complaint#2 |
| user-area = defined | label = chart*m-hist#2 |
| user-area = defined | label = chart*diagnosis#2 |
| user-area = defined | label = chart*diagnosis*1#2 |
| user-area = defined | label = chart*diagnosis*2#2 |
| user-area = defined | label = chart*diagnosis*3#2 |
| user-area = defined | label = chart*tmt#2 |
| user-area = defined | label = chart*lab-test#2 |
| user-area = defined | label = chart*lab-test*788-1#3 |
| user-area = defined | label = chart*lab-test*790-2#3 |
| user-area = defined | label = chart*lab-test*790-45#3 |
| user-area = defined | label = close#8 |

FIG.4

☐
Begin

| 1 | 2 |    | 1 | 2̌ |    | 1 | 2 |    | 1 | 2 |
|---|---|    |---|---|    |---|---|    |---|---|
| 3̌| 4 |    | 3 | 4 |    | 3 |4̌ |    | 3̌| 4 |

—132

Patient Name: _Patient_ ~—132

Chief Complaint: _headache_ ⌒—132
_back pain_

Medical History: _none_ ~—132

Diagnosis: 1 _strained back muscle_ ⌒—132
2 _strained neck_
3

Treatment: 1 _aspirin_ ⌒—132
2 _ice_
3

LAB Tests: ☐ Test A, 788.1
132—☑ Test B, 790.2
☐ Test C, 790.45

☑
Finalize

Contextual info 184 { area label = diagnosis
area type = image
format = svg
end time = 10040 } 166 contextualized data element root info 182 { SVG data set }

Contextual info 184 { area label = diagnosis_1
area type = image
format = svg
end time = 10037 } 168 contextualized data element root info 182 { SVG data set }

Contextual info 184 { area label = diagnosis_2
area type = image
format = svg
end time = 10040 } 170 contextualized data element root info 182 { SVG data set }

Contextual info 184 { area label = tmt
area type = image
format = svg
end time = 10050 } 172 contextualized data element root info 182 { SVG data set }

Contextual info 184 { area label = lab_test
area type = image
format = svg
end time = 10060 } 174 contextualized data element root info 182 { SVG data set }

Contextual info 184 { area label = lab_test_790_2
area type = alphanumeric
end time = 10070 } 176 contextualized data element root info 182 { < 790.2 > }

FIG.6/2

SYSTEM AND METHOD FOR MANAGING FORM-GENERATED DATA

CROSS-REFERENCE TO RELATED APPLICATIONS

This application is entitled to the benefit of provisional U.S. Patent Application Ser. No. 60/758,842, filed Jan. 13, 2006 and provisional U.S. Patent Application Ser. No. 60/810,248, filed Jun. 2, 2006, the disclosures of which is incorporated by reference herein in its entirety.

FIELD OF THE INVENTION

The invention relates generally to managing form-generated data, and in particular, to managing form-generated data that is related to a patient encounter and used by one or more electronic medical record (EMR) and/or electronic health record (EHR) applications to perform a function such as patient/insurance billing, case management, and/or order fulfillment.

BACKGROUND OF THE INVENTION

Typical EMR/EHR software applications produced for use by front-line healthcare workers follow a flow-based model. That is, the healthcare provider is required to navigate through a series of windows according to a pre-established flow and then enter data related to a patient encounter at the appropriate window. Because the data is entered at a window that is part of a pre-established flow, the EMR/EHR application knows exactly what type of data to expect at each data entry point. For example, if a healthcare worker navigates to a diagnosis window and checks a box labeled "sprained ankle," the EMR/EHR application is coded to identify the input data as a sprained ankle. A drawback to applying flow-based software applications to the healthcare industry is that the flow produced by the software developer and coded into the application may not match the actual work flow of a healthcare worker.

Electronic writing systems have been developed to translate a user writing on a paper form to electronic data. Translating user writing on a paper form to electronic data can help free a healthcare worker from the requirements of rigid flow-based EMR/EHR applications. Typical electronic writing systems track the pen strokes of a user writing on a form and generate a data set that represents the user's pen strokes. The pen stroke data set is then used to create an electronic image of the marked up form. The electronic image can be viewed on a remote computer to perform various tasks that need to be completed subsequent to a patient encounter (e.g., patient/insurance billing, case management, order fulfillment, etc.).

While creating an electronic image of a marked up form on a remote computer allows subsequent electronic access to the marked up forms, to glean useful data from the user writing on the form, a person viewing the electronic image must manually convert the user writings to useable data, by for example, keying in data from check boxes. Alternatively, useful data can be gleaned from the pen stroke data set by programming the EMR/EHR application to relate pen stroke data directly to a software routine or action. For example, a software developer must hardcode that a check at the coordinates of a box labeled "sprained ankle" translates to the diagnosis of a sprained ankle. This process is very inefficient for a software developer because it requires the developer to have specific knowledge of the layout of every information field on every form that is to be used with the EMR/EHR application. Further, even if the developer does attempt to hardcode every field of every form to a corresponding routine or action, it is often desirable or necessary to change the layout of a form to accommodate new and/or different information. If an EMR/EHR application is directly dependent on the layout of a form, the EMR/EHR application must be reprogrammed to reflect each subsequent layout change.

Further, different electronic writing systems exist which use different techniques to translate user writings to a pen stroke data set. Consequently, the same information on a form may result in a different pen stroke data set depending on which electronic writing system is used to track the pen strokes and therefore an EMR/EHR application must be coded to deal with all the possible pen stroke data sets for each electronic writing system that is to be supported by the EMR/EHR application.

SUMMARY OF THE INVENTION

A system and method for managing form-generated data related to a patient encounter involves translating location information related to a user writing on a form into a contextualized data element that includes contextual information. The contextual information helps to explain and/or give meaning to the user writing. For example, contextual information may include a descriptive name, an identification of data type, healthcare classification information, taxonomic information, an indication of the patient, an indication of the person that wrote on the form, and/or an indication of the date and time at which the writing occurred. The contextual information is then used by an EMR/EHR application to perform a function such as patient/insurance billing, case management, order fulfillment, etc.

By translating location information related to a user writing into a contextualized data element, EMR/EHR applications are insulated from the specific layout of paper forms that are used by healthcare workers, thereby allowing EMR/EHR applications to be developed independent of the actual layout of the forms. Additionally, the translation of location information to contextualized data elements insulates EMR/EHR applications from the specifics of the electronic writing system so that the EMR/EHR applications can be developed independent of the type of electronic writing system that is used.

Other aspects and advantages of the present invention will become apparent from the following detailed description, taken in conjunction with the accompanying drawings, illustrating by way of example the principles of the invention.

BRIEF DESCRIPTION OF THE DRAWINGS

FIG. 2 depicts a form that is intended to be written on by a user such as a front-line healthcare worker.

FIG. 4 depicts a mapping data set that corresponds to the labeled designated information fields depicted in FIG. 3.

FIG. 5 depicts exemplary user writings on the form depicted in FIGS. 2 and 3, which are translated to contextualized data elements as described below.

Throughout the description, similar reference numbers may be used to identify similar elements.

DETAILED DESCRIPTION OF THE INVENTION

Figure 1:
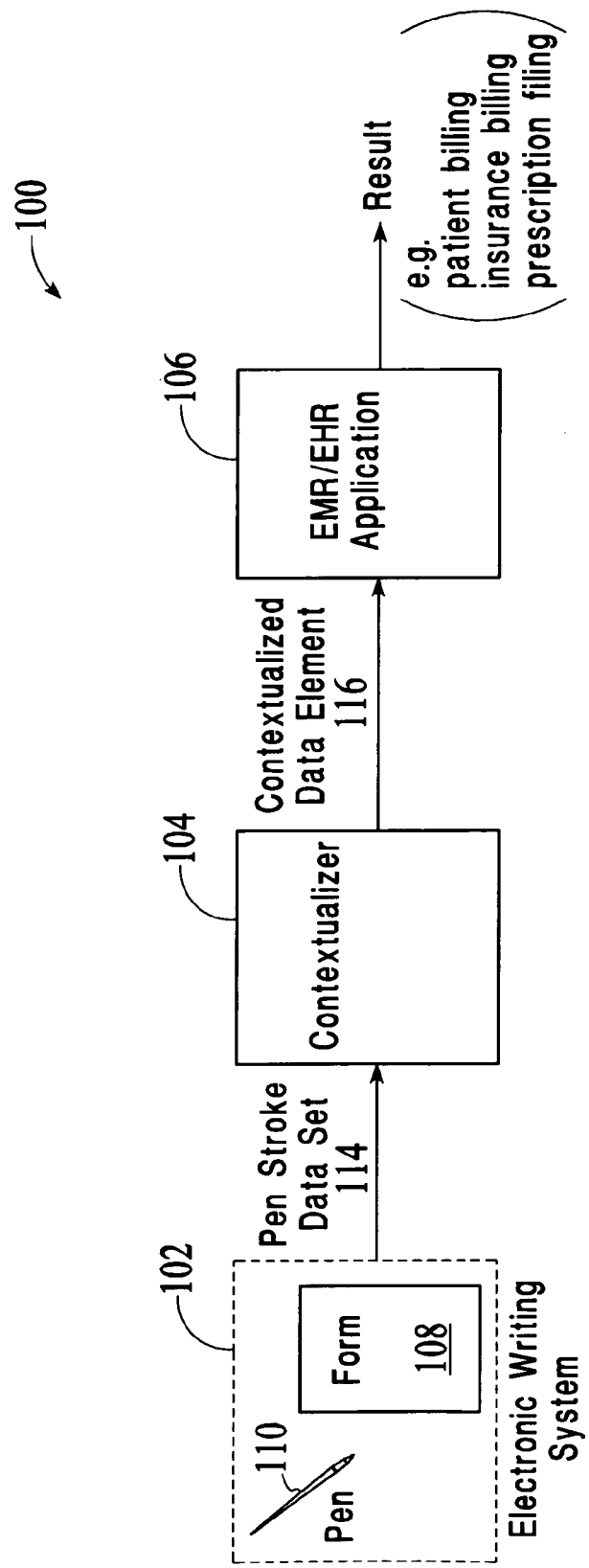
FIG. 1 depicts a system for managing form-generated data related to a patient encounter.

FIG. 1 depicts a system 100 for managing form-generated data related to a patient encounter. The system includes an electronic writing system 102, a contextualizer 104, and an EMR/EHR application 106. The electronic writing system includes a form 108 and a writing instrument such as a pen. The electronic writing system generates electronic location information that is representative of a user writing on the form. For example, the electronic writing system generates a data set that defines the pen strokes of a user writing on the form. In an embodiment, the location information is generated as a pen stroke data set 114 that includes a collection of vectors that define the pen strokes made by a user, with the vectors being linked to coordinates on the form.

Various different types of electronic writing systems can be used to generate location information related to a user writing on a surface such as a piece of paper or a form. Exemplary electronic writing systems include:

1) a camera-based pen system that works in conjunction with special encoding on a piece of paper. In general, these camera-based pen systems include a pen with an optical sensor (camera) in the end and a paper that has a position-coding pattern which is detectable by the optical sensor. The absolute position of the pen on the paper is determined by monitoring the position-coding pattern through the optical sensor as the pen is used to write on the paper. Various aspects of camera-based pen systems are described, for example, in U.S. Pat. Nos. 6,548,768, 6,570,104, 6,663,008, 6,667,695, 6,674,427, and 6,899,966;

2) a radio frequency (RF) or infrared (IR) detection system that uses triangulation to track the movement of a pen around the x-y plane of a piece of paper. In one embodiment, the detection system is clipped onto a piece of paper and RF or IR based triangulation is used to track the movement of a pen as a user writes on the paper. The tracked movement is then recorded in the detection system for subsequent transfer to a more powerful computer system; and 3) a tablet computer system that displays a form on a computer screen and detects contact with the screen by a stylus to track the movement of the stylus as a user writes on the screen.

The contextualizer 104 converts location information (e.g., a pen stroke data set) from the electronic writing system into at least one contextualized data element 116 that can be used by the EMR/EHR application 106 to perform a function such as patient/insurance billing, case management, order fulfillment, and/or clinical studies, etc. In an embodiment, a contextualized data element includes root information and contextual information. The root information is the information that is intended to be conveyed through the user writing. The root information may include, for example, pen stroke coordinates if the information to be conveyed is an image of the user writings and/or alphanumeric information if the information to be conveyed is simply a numeric code or a word. The contextual information is information that provides context to the root information. For example, contextual information is information that explains and/or gives meaning to the root information. As is described in more detail below, the contextual information may include a region label, an area label, an indication of the root data type, temporal information, an indication of the patient to which the root information is associated, and/or an indication of the user that made the writings on the form. The writing on a form can be translated to one or more contextualized data elements. Multiple contextualized data elements can be combined into an encounter data set, which characterizes a patient encounter.

The contextualized data elements are used by the EMR/EHR application to perform a function. The EMR/EHR application performs functions based on data collected via the electronic writing system 102. Exemplary functions performed by the EMR/EHR application include, but are not limited to, patient/insurance billing, case management, and order fulfillment.

In accordance with the invention, the EMR/EHR application uses at least one contextualized data element to perform a function. Although only one EMR/EHR application is depicted in FIG. 1, multiple EMR/EHR applications may exist, each of which performs a function using contextualized data elements from the contextualizer. The multiple EMR/EHR applications may use the same contextualized data element(s), different contextualized data elements, or any combination thereof.

The process of translating location information related to a user writing to a contextualized data element is now described with reference to FIGS. 2-6. FIG. 2 depicts a form that is intended to be written on by a user such as a front-line healthcare worker (e.g., a doctor or nurse). The form can be a paper form, an image of a form on a display screen (such as on a tablet computer), or some other type of form, which enables the generation of electronic location information that identifies the location of a user writing on the form. The form includes designated information fields at different locations that are intended to be written on to convey certain information. The nature of the information to be conveyed within a designated information field is typically indicated to various degrees on the form. Some designated information fields are labeled with a descriptor that indicates the type of information that is to be entered into a designated information field. For example, the descriptor "Patient Name" on the form of FIG. 2 indicates that a patient name should be entered on the corresponding line. Other designated information fields (e.g., check boxes) are labeled with descriptors that indicate the information that is to be conveyed if the designated information field is checked. For example, the descriptors "Lab Tests" and "Test A, 788.1" on the form of FIG. 2 indicate that the corresponding designated information field (e.g., check box 150) relates to "Test A, 788.1". Other designated information fields, for example, the pin pads on the form of FIG. 2 indicate the numeric values associated with each designated information field. Still other designated information fields, for example, the "Begin" and "Finalize" designated information fields on the form of FIG. 2 correspond to specific functions that are to be performed when the field is marked. Although some examples of designated information fields are described with reference to FIG. 2, other types of designated information fields are possible. Additionally, although some examples of descriptors are described, other types of descriptors, including non-alphanumeric descriptors are possible. For example, an image of a human body on a form may be a descriptor that indicates the image is to be written on to convey certain information.

Figure 3:
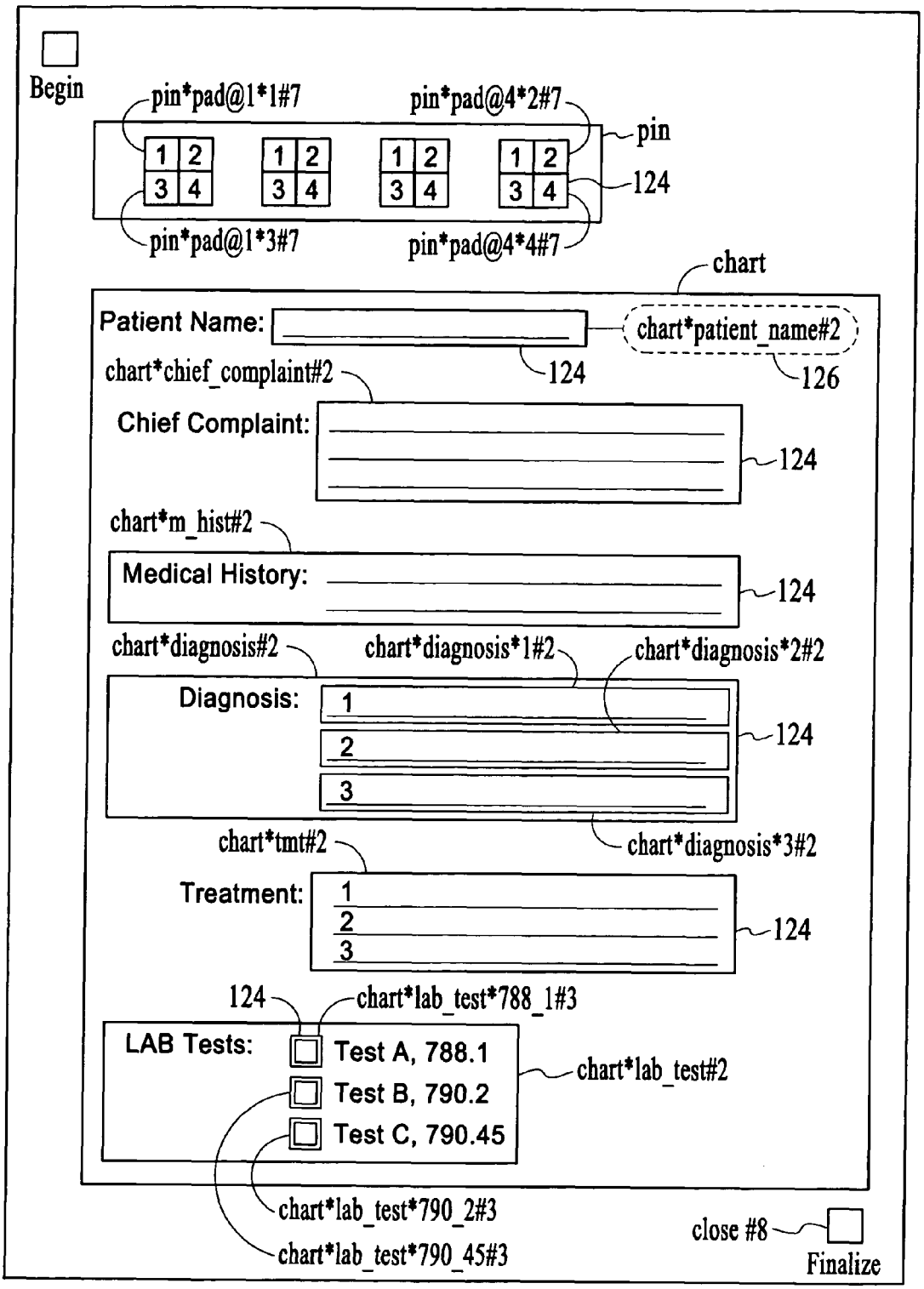
FIG. 3 illustrates designated information fields within the form of FIG. 2 along with their associated labels.

In order to translate location information into contextualized data elements, the designated information fields on the form of FIG. 2 are assigned labels. FIG. 3 illustrates designated information fields 124 within the form of FIG. 2 along with their associated labels 126. In accordance with an embodiment of the invention, the label associated with each designated information field explains and/or gives meaning to the corresponding designated information field. Typically, a label has a meaning that corresponds to the descriptor on the form. For example, the label for the designated information field "Patient Name" may include the words "patient" and "name". The labels may include taxonomic information that indicates, for example, a relationship of the designated information field relative to other designated information fields. Referring to FIG. 3, the form includes a large region labeled as "chart" and multiple sub-regions labeled as "chief_complaint", "m_hist", "diagnosis", "tmt", and "lab_test". Sub-region "diagnosis" includes sub-regions "1", "2", and "3", and sub-region "lab_test" includes sub-regions "788_1", "790_2", and "790_45". In the embodiment of FIG. 3, taxonomic information is conveyed by forming a label that is a composite of regions and sub-regions in order from the most general region to the most specific region. For example, the label "chart*diagnosis*1" conveys that the designated information field is in region "chart", sub-region "diagnosis", and sub-region "1", where sub-region "diagnosis" is a sub-region of "chart" and sub-region "1" is a sub-region of "diagnosis". The label may also include root information. For example, in the label "chart*lab_test*790$_{13}$ 2#3," the root information is "790_2", which translates to the number 790.2.

In an embodiment, the labels associated with the designated information fields include an element or elements that correspond to standardized medical terms and/or codes and/or accepted terminology and/or codes used in EMR/EHR applications. For example, labels may incorporate: International Classification of Diseases (ICD) codes, for example, ICD version 9 (ICD-9) codes and Current Procedure Terminology (CPT) codes, both of which are published by the American Medical Association (AMA). An exemplary label could incorporate the code "845.00," which is the ICD-9 code for a sprained ankle. The labels may have a structure that corresponds to accepted medical classifications.

The label of a designated information field may also identify the type of root information that is to be gleaned from a user writing in the designated information field. For example, the root information gleaned from a user writing in the designated information field may be:

1) pen stroke information that can be used to create an electronic image of the user writing on the form;

2) alphanumeric information, for example, a name or number that corresponds to a checked box or alphanumeric information that is recovered via character recognition; and 3) pin pad information, for example, the numbers 0-9, a decimal point, and a cancel pin, which can be used to enter specific numerical values.

In another embodiment, the label of a designated information field may represent a rule or function that is to be carried out. For example, the label of a designated information field my trigger a function such as indicating that the writing on a form is to be forwarded to an application (e.g., a "finalize" function).

In the embodiment of FIG. 3, the label identifies the type of root information using a numeric code value that follows the "#" sign in the label. In this embodiment, the value "2" indicates that the root information is a pen stroke data set, the value "3" indicates that the root information is alphanumeric information, and the value "7" indicates that the root information is an entry from a pin pad, which includes the numbers 0-9, a decimal point, and a cancel pin. Although one example of a technique for identifying data types is identified, other techniques can be used.

In conjunction with labeling the designated information fields as described above with reference to FIG. 3, location translations are generated for the designated information fields. In an embodiment, a location translation associates an area on a form (i.e., a designated information field) with a label. The area on the form can be defined by a set of values related to the coordinate system used by the electronic writing system. For example, a camera-based electronic writing system may define areas on a form by top, left, height, and width values, where the top value indicates the distance of a coordinate point from the top edge of the form, where the left value indicates the distance of the coordinate point from the left edge of the form, and where the height and width values define the height and width dimensions of a box which has a corner at the coordinate point. A set of location translations that cover a particular form is referred to herein as a "mapping data set." FIG. 4 depicts a mapping data set 128 that corresponds to the labeled designated information fields depicted in FIG. 3. Referring to FIG. 4, each location translation 130 of the mapping data set includes an identification of the user area and an identification of the corresponding label. In FIG. 4, the generic term "defined" is used to represent a definition of the user area by any appropriate means. For example, a rectangular user area may be defined by the coordinates of a starting point, a height dimension, and a width dimension. In an embodiment, the coordinates of the starting point are measured from the top and left edges of the form, the height dimension extends down from the starting point, and the width dimension extends to the right of the starting point. Although one technique for defining the area of a designated information field is described, other techniques can be used.

In an embodiment, a location translation is generated through a graphical user interface that first provides an image of the form. A user then identifies a designated information field against the background of the form. In particular, the user sets the size and location of the designated information field relative to the form and the corresponding coordinates of the designated information field, which will be used for location translation, are calculated. Once the size and location of the designated information field is identified, the designated information field is assigned a label.

If the physical location of a designated information field changes on a form, the location translation for the designated information field can be changed to reflect the new location. In particular, a change in the location of a designated information field is accommodated simply by changing the defined user area of a location translation. That is, no change in the label is required to accommodate a change in the location of a designated information field. For example, referring to FIGS. 3 and 4, if the locations of designated information fields "Medical History" (labeled as "chart*m_hist#2") and "Treatment" (labeled as "chart*tmt#2") needed to be swapped on the form, the definition of the two user areas would be changed to reflect their new locations on the form but their respective labels would stay the same. Leaving the labels the same ensures that changes to the physical layout of forms has no effect on the EMR/EHR applications.

Once the designated information fields of a form have been labeled and a mapping data set established, the contextualizer 104 can translate location information related to user writings into contextualized data elements. FIG. 5 depicts exemplary user writings 132 on the form depicted in FIGS. 2 and 3, which are translated to contextualized data elements as described below. In an embodiment, contextualized data elements are generated only for those designated information fields that receive user writing. That is, the user writing triggers the generation of a contextualized data element.

Figure 6:
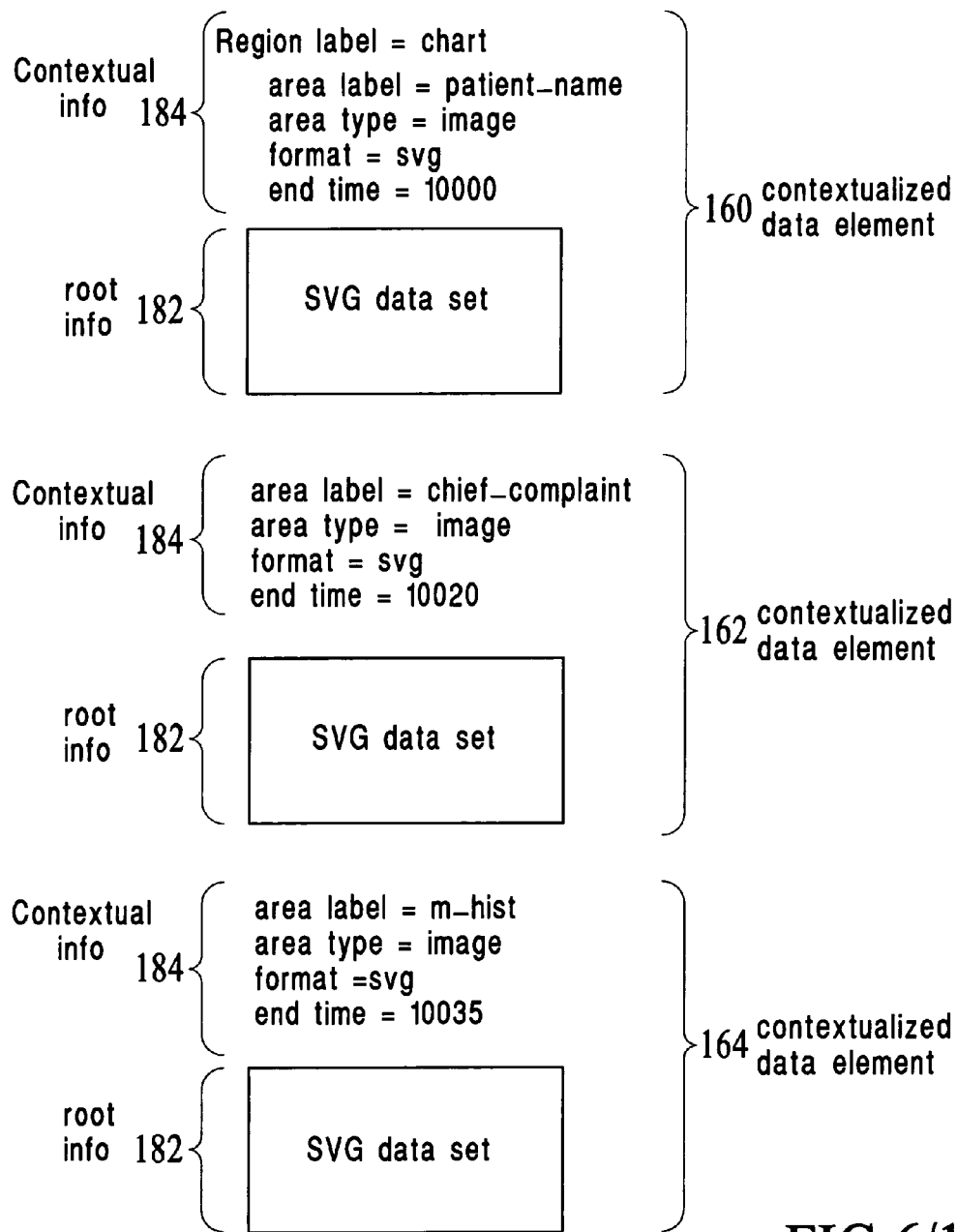
FIG. 6 depicts an example of the contextualized data elements that result from the user writings depicted in FIG. 5.

In operation, user writings 132 on the form of FIG. 5 are converted into location information by an electronic writing system 102, for example, a camera-based electronic pen system. In an embodiment, the location information is provided to the contextualizer 104 as a pen stroke data set. The contextualizer translates the pen stroke data set into contextualized data elements using the mapping data set 128 described above with reference to FIGS. 3 and 4. Pen strokes that fall within a designated information field are translated to at least one contextualized data element and FIG. 6 depicts an example of the contextualized data elements 160-176 that result from the user writings depicted in FIG. 5. The multiple contextualized data elements combine to form an encounter data set 180, which characterizes an encounter between a patient and a healthcare worker.

Referring to FIG. 6, the first contextualized data element 160 results from user writings 132 in the designated information field labeled "chart*patient_name#2". The contextualized data element includes root information 182 and contextual information 184. The root information is the information that is intended to be conveyed by the user writing. In this contextualized data element, the root information is an .svg data set that represents the user writing in the "Patient Name" field, where .svg is a scalable vector graphics (SVG) file format as defined by the World Wide Web Consortium. The .svg data set can be used to create an electronic image of the user writing in the designated information field. The contextual information is information that adds context to the root information, for example, information that explains or gives meaning to the root information. In this contextualized data element, the contextual information includes a region label, an area label, an area type, format, and end time. The contextual information entitled "region label" identifies the region to which the root information belongs. In the example of FIG. 6, the region label "chart" indicates that the root information belongs to the "chart" region on the form. The contextual information entitled "area label" identifies the sub-region to which the root information belongs. In the example of FIG. 6, the area label "patient_name" indicates that the root information was found in the "patient_name" sub-region on the form. The contextual information entitled "area type" identifies the type of root information that is included in the contextualized data element. In the example of FIG. 6, the area type "image" indicates that the root information is data that represents an image of the user writing within the designated information field. The contextual information entitled "format" identifies the format of the root information. In the example of FIG. 6, format "svg" indicates that the root information is in .svg file format. The contextual information entitled "end time" identifies the time at which the user writing in the designated information field ended. The end time can be represented in a suitable temporal format and the end time of "10000" is provided only as an example.

Contextualized data elements 162-176 have basically the same structure as contextualized data element 160. Although each subsequent contextualized data element does not repeat the region label, the region label is assumed to be the same for all subsequent contextualized data elements until a new region label is identified. In an alternative embodiment, common contextual information can be repeated for each contextualized data element.

Some user writings 132 can be translated into more than one contextualized data element. For example, the user writings in the designated information fields labeled "chart*diagnosis*1" and "chart*diagnosis*2" are represented in the "diagnosis_1" and "diagnosis_2" contextualized data elements 168 and 170, respectively, and the user writing in both fields is represented in the more general "diagnosis" contextualized data element 166.

A contextualized data element can include various types of contextual information. For example, contextual information may include an indication of the patient to which the root information belongs, an indication of the healthcare worker that made the user writings on the form, an indication of the instrument that was used to make the user writings (e.g., a pen ID), an indication of the date of the user writings, a transaction identifier and/or insurance information. Further, certain contextual information can be associated with multiple contextualized data elements in an encounter data set. Referring again to FIG. 6, certain contextual information is associated with each contextualized data element in the encounter data set. For example, each contextualized data element includes the same TopicID, the same transaction ID, the same date, and the same pen ID. In this example, the TopicID is an identifier that is cross-referenced to a particular patient, the transaction ID is a unique identifier that encompasses the instant writings, the date is the date on which the user writings were made, and the pen ID is the serial number of the pen that was used to write on the form.

As described above, the root information 182 is not always pen stroke data that is used to create an image of the user writings on the form. In an embodiment, the root information is alphanumeric data that is gleaned from the pen stroke data. For example, the root information is a numeric code that represents a particular diagnosis or treatment that is gleaned from a checked box on a form. Referring to FIG. 6, a contextualized data element that includes alphanumeric root information is identified as contextualized data element 176. The contextualized data element is generated in response to the user writing in the designated information field labeled "chart*lab_test*790_2#3". Referring to contextualized data element 176, the contextual information "lab_test_790_2" indicates that the root information is associated with a lab test having the code "790.2", the contextual information "alphanumeric" indicates that the root information is alphanumeric, and the contextual information "10070" indicates the end time of the user writing in the designated information field. The root information is the number 790.2. Often times alphanumeric root information is a number or word that is generally known in the healthcare field and used by healthcare workers and/or EMR/EHR applications to identify, for example, a particular diagnosis, treatment, procedure, medication, medical apparatus, patient characteristic, billing rate, etc.

In accordance with an embodiment of the invention, an EMR/EHR application utilizes contextual information in the contextualized data elements to perform a function that is related to the user writing on a form. How the contextual information is utilized to perform a function is entirely dependent on the function that is to be performed. In one embodiment, the contextual information is used by the EMR/EHR application to identify the contextualized data element. For example, the contextualized data element related to the "Chief Complaint" designated information field is called by an EMR/EHR application using the label "chief_complaint" instead of by identifying the corresponding coordinate set that identifies the user area boundaries. In another embodiment, the contextual information is used by the application to identify the patient associated with the contextualized data element, the writing instrument that was used, the type of root data that is included in the contextualized data element, and/or the date and time of the user writing.

In an embodiment, the contextualizer is part of a middleware application that helps to distribute contextualized data elements to EMR/EHR applications. In an embodiment, the middleware and EMR/EHR applications exchange information according to a publish/subscribe protocol. In particular, the EMR/EHR applications request certain form-generated information that is related to a patient encounter (i.e., subscribe) and the middleware application ensures that any information meeting the application's request is provided (i.e., published) to the application. Because contextualized data elements are provided in a publish/subscribe environment, there is no need to maintain a continuous connection between the middleware and the application once a subscription request is made.

Figures 7, 8:
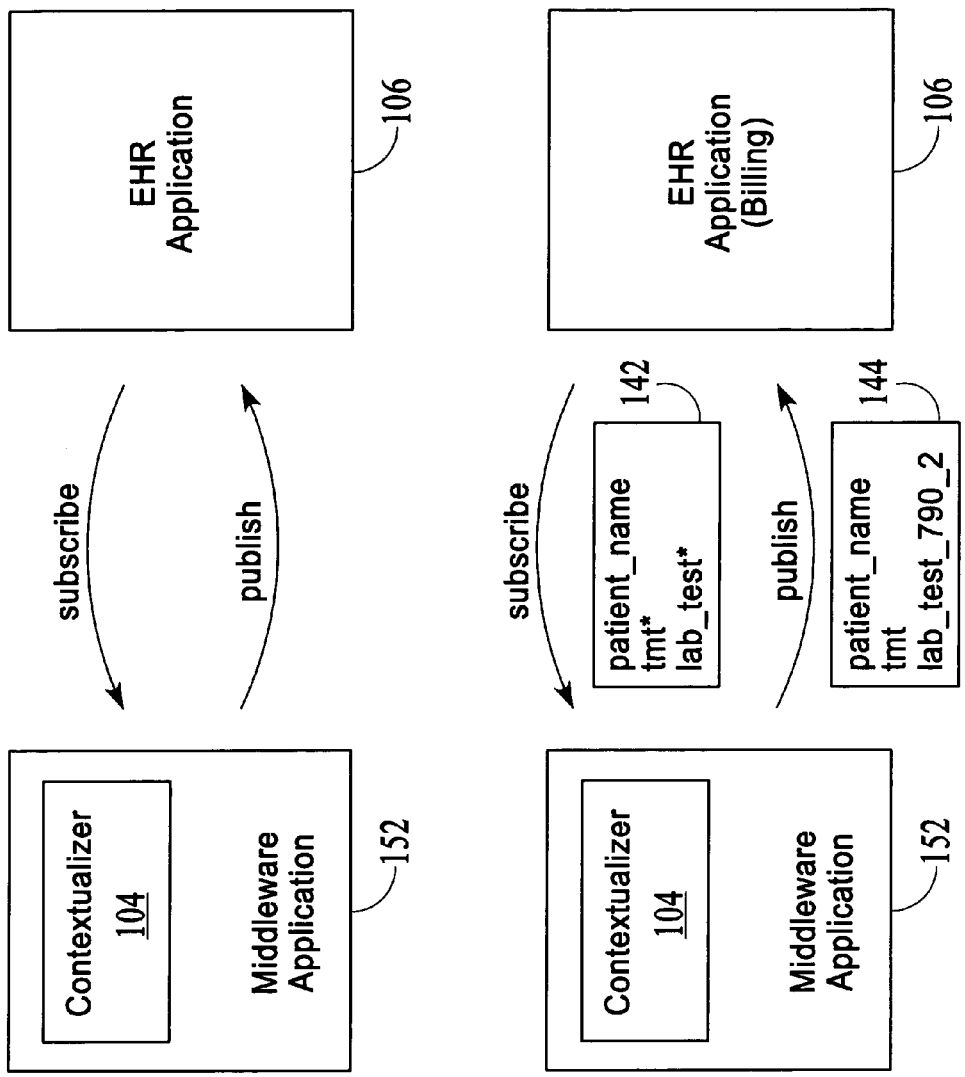
FIG. 7 illustrates publish and subscribe operations between a middleware application and an EMR/EHR application as described above.
FIG. 8 illustrates a subscription request for all information in sub-regions "patient_name", "tmt", and "lab_test" of the form described above with reference to FIGS. 3-6.

FIG. 7 illustrates publish and subscribe operations between a middleware application 152 and an EMR/EHR application 106 as described above. In an embodiment, the subscription request identifies all of the information that the EMR/EHR application desires to receive. The information desired by the EMR/EHR application is identified at least in part using the contextual information generated by the contextualizer 104. When the middleware application determines that it has information meeting the subscription request, the requested information is published to the EMR/EHR application. In an embodiment, the requested information is published to an EMR/EHR application as contextualized data elements in a .xml file format.

Even though multiple contextualized data elements may be grouped together into a single encounter data set, the individual contextualized data elements can be parsed and treated separately for purposes of distribution to the EMR/EHR application. That is, EMR/EHR applications can subscribe to a subset of the contextualized data elements that make up an encounter data set. Additionally, different EMR/EHR applications may subscribe to different information and the contextual information associated with the contextualized data elements allows the contextualized data elements to be managed as distinct information elements.

FIG. 8 illustrates a subscription request 142 for all information in sub-regions "patient_name", "tmt", and "lab_test". FIG. 8 also illustrates information from the contextualized data element of FIG. 6 that matches the subscription request. The information 144, which is published to the EMR/EHR application, includes the contextualized data elements "patient_name", "tmt", and "lab_test_790_2". Given the labeling structure associated with the contextualized data elements, the specificity of a subscription request can be controlled through label selection. For example, a subscription request for all information having at least the "chart*" label will include more information than a subscription request for all information having at least the "chart*lab_test*" label.

In an environment that includes different EMR/EHR applications for different functions (e.g., three separate EMR/EHR applications for patient/insurance billing, case management, and order fulfillment), the middleware application distributes to the different EMR/EHR applications only those contextualized data elements that are requested by the applications.

Figure 9:
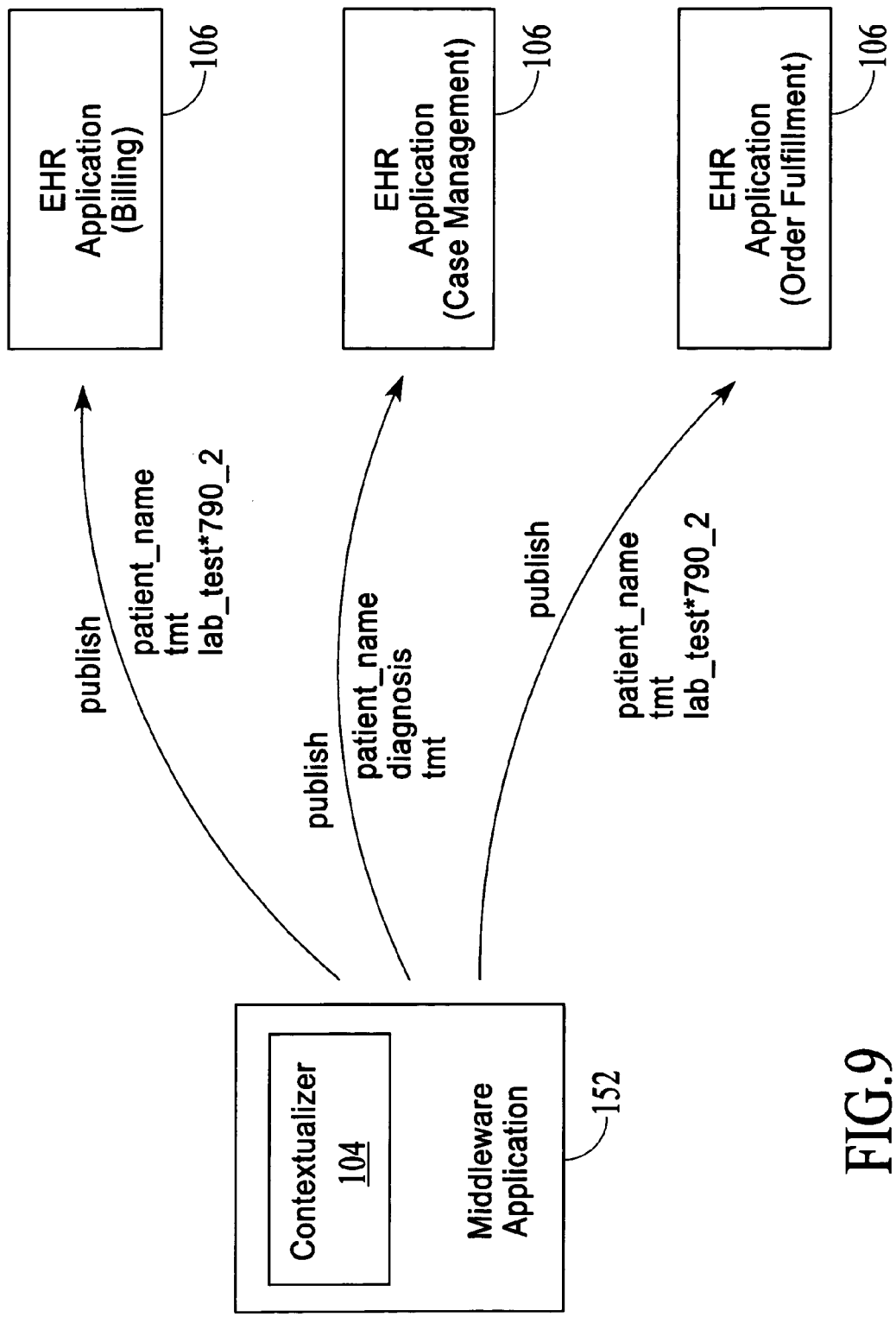
FIG. 9 illustrates the distribution (publishing) of contextualized data elements to different EMR/EHR applications.

FIG. 9 illustrates the distribution (publishing) of contextualized data elements to different EMR/EHR applications 106. As illustrated in FIG. 9, each EMR/EHR application receives a different set of contextualized data elements from the encounter data set. The set of contextualized data elements that is received by each EMR/EHR application is a function of the subscription requests made by each EMR/EHR application. Various levels of subscription controls can be managed by the middleware application to ensure that applications receive only information that the applications are authorized to receive.

Because the location information that identifies the location of user writings on a form has been translated to contextualized data elements, the EMR/EHR applications can be configured to operate based on contextual information instead of raw location information such as coordinates. Because the EMR/EHR applications operate based on contextual information instead of raw location information, the EMR/EHR applications are effectively independent of the physical layout of a form. That is, if a designated information field is moved to a new physical location on a form, only the location translation related to the designated information field needs to be changed to reflect the new physical location of the designated information field. That is, the defined user area is changed to reflect the new location on the form while the label remains the same. The change in location requires no modification to the EMR/EHR application. This layout-independence allows EMR/EHR applications to be developed without concern for the physical layout of forms.

Figure 10:
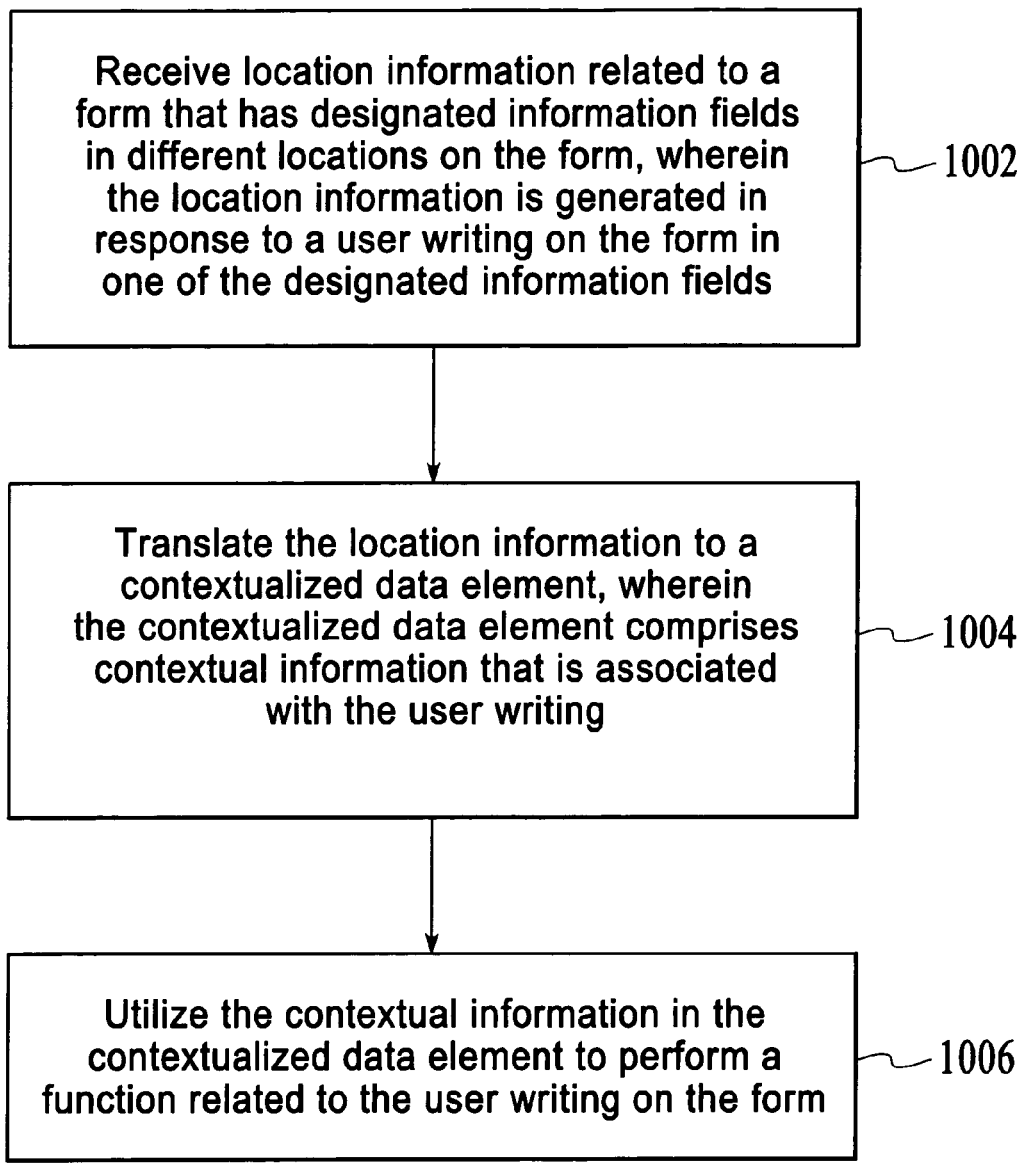
FIG. 10 depicts a method for managing form-generated data related to a patient encounter in accordance with an embodiment of the invention.

FIG. 10 depicts a method for managing form-generated data related to a patient encounter. At block 1002, location information related to a form, which has designated information fields in different locations on the form, is received, wherein the location information is generated in response to a user writing on the form in one of the designated information fields. At block 1004, the location information is translated to a contextualized data element, wherein the contextualized data element comprises contextual information that is associated with the user writing. At block 1006, the contextual information in the contextualized data element is utilized to perform a function related to the user writing on the form.

A method in accordance with the present invention may also be implemented, for example, by operating a computer system to execute a sequence of machine-readable instructions. The instructions may reside in various types of computer readable media. In this respect, another embodiment of the invention involves a programmed product, comprising computer readable media tangibly embodying a program of machine readable instructions executable by a digital data processor to perform a method for discarding routes from a router. This computer readable media may comprise, for example, RAM contained within the contextualizer. Alternatively, the instructions may be contained in another computer readable media such as a magnetic data storage diskette and directly or indirectly accessed by the contextualizer. Whether contained in the computer system or elsewhere, the instructions may be stored on a variety of machine readable storage media, such as a DASD storage (e.g. a conventional "hard drive" or a RAID array), magnetic tape, electronic read-only memory, an optical storage device (e.g., CD ROM, WORM, DVD, digital optical tape), paper "punch" cards, or other suitable computer readable media including transmission media such as digital, analog, and wireless communication links. In an illustrative embodiment of the invention, the machine-readable instructions may comprise lines of compiled C, C++, or similar language code commonly used by those skilled in the programming for this type of application arts.

Although the system and method for managing form-generated data is described with reference to a patient encounter, the system and method could be applied to other instances where forms are used to collect information that is later used by a software application to perform a function such as billing, order fulfillment, scheduling, etc.

Although specific embodiments of the invention have been described and illustrated, the invention is not to be limited to the specific forms or arrangements of parts as described and illustrated herein. The invention is limited only by the claims.

What is claimed is:

1. A system for managing form-generated data related to a patient encounter, the system comprising:
   a form having designated information fields at different locations on the form;
   an electronic writing system configured to generate location information that identifies the location of a user writing on the form;
   a contextualizer configured to translate location information related to the user writing to a contextualized data element, wherein the contextualized data element comprises contextual information that is associated with the user writing, wherein the contextualizer includes a mapping data set that maps user areas on the form to labels that are associated with the designated information fields and wherein the contextualizer is configured to identify a label from the location information by comparing the location information to the mapping data set, the contextualized data element comprising the label; and
   an Electronic Medical Record (EMR)/Electronic Health Record (EHR) application that utilizes the label in the contextualized data element to perform a function that is related to the user writing on the form;
   wherein the contextualized data element is distributed to the EMR/EHR application via a publish/subscribe protocol in which the EMR/EHR application subscribes to a specific contextualized data element by identifying the label associated with the contextualized data element.

2. The system of claim 1 wherein the location information comprises a pen stroke data set that represents the user writing on the form.

3. The system of claim 1 wherein the contextualized data element comprises root information and contextual information, wherein the contextual information explains or gives meaning to the root information.

4. The system of claim 3 wherein the root information is one of a medical code and an image file that is representative of at least a portion of the user writing on the form.

5. The system of claim 1 wherein the label corresponds to accepted medical terms.

6. The system of claim 1 wherein the label conveys medical taxonomy.

7. The system of claim 1 wherein the label comprises a standardized medical code.

8. The system of claim 1 wherein the label comprises one of an International Classification of Disease (ICD) and a Current Procedure Terminology (CPT) code.

9. The system of claim 1 wherein the contextualizer is configured such that the mapping data set is changeable in response to changes in the locations of the designated information fields on the form.

10. The system of claim 1 wherein the contextual information comprises temporal information.

11. The system of claim 1 wherein the contextualized data element comprises a region label, an area label, and an area type indicator.

12. The system of claim 1 wherein the contextual information includes standardized medical terms.

13. The system of claim 1 wherein the performed function includes one of patient/insurance billing for services rendered related to the patient encounter, case management related to the patient encounter, and order fulfillment related to the patient encounter.

14. The system of claim 1, wherein the labels include taxonomic information.

15. The system of claim 1, wherein the labels include taxonomic information that indicates a relationship of the designated information fields relative to each other.

16. The system of claim 15, wherein the taxonomic information in the labels is a composite of a region and a sub-region.

17. A method for managing form-generated data related to a patient encounter, the method comprising:
   receiving location information related to a form that has designated information fields in different locations on the form, wherein the location information is generated in response to a user writing on the form in one of the designated information fields;
   translating the location information to a contextualized data element, wherein the contextualized data element comprises contextual information that is associated with the user writing, wherein translating the location information to a contextualized data element comprises using the location information to identify a label by comparing the location information to a mapping data set that maps user areas on the form to labels that are associated with the designated information fields, and wherein the contextualized data element comprises the label; and
   utilizing the label in the contextualized data element to perform a function related to the user writing on the form, wherein the function is performed by an EMR/EHR application and wherein the contextualized data element is distributed to the EMR/EHR application via a publish/subscribe protocol in which the EMR/EHR application subscribes to a specific contextualized data element by identifying the label associated with the contextualized data element.

18. The method of claim 17 wherein the location information comprises a pen stroke data set that represents the user writing on the form.

19. The method of claim 17 wherein the contextualized data element comprises root information and contextual information, wherein the contextual information explains or gives meaning to the root information.

20. The method of claim 19 wherein the root information is one of a medical code and an image file that is representative of at least a portion of the user writing on the form.

21. The method of claim 17 further comprising generating an encounter data set comprising multiple contextualized data elements, which together characterize a patient encounter.

22. The method of claim 21 wherein the encounter data set comprises:
   an indication of the patient associated with the patient encounter;
   an indication of the substance of the patient encounter; and
   an indication of the time of the patient encounter.

23. The method of claim 21 wherein the encounter data set comprises an indication of the user that made the user writing on the form.

24. The method of claim 17 further comprising changing the mapping data set in response to changes in the locations of the designated information fields on the forms.

25. The method of claim 17 wherein utilizing the contextual information in the contextualized data element to perform a function comprises performing a function related to patient/insurance billing for services rendered related to the patient encounter, case management related to the patient encounter, and order fulfillment related to the patient encounter.

26. The method of claim 17, wherein the labels include taxonomic information.

27. A system for managing form-generated data related to a patient encounter, the system comprising:
   a contextualizer configured to translate location information related to a user writing to a contextualized data element, wherein the contextualized data element comprises root information and a label, wherein the label explains or gives meaning to the root information;
   wherein the location information is received from an electronic writing system that is configured to generate location information that identifies the location of the user writing on a form that has designated information fields at different locations on the form;
   wherein the contextualizer includes a mapping data set that maps user areas on the form to labels that are associated with the designated information fields and wherein the contextualizer is configured to identify a label from the location information by comparing the location information to the mapping data set; and
   wherein the contextualizer is configured to distribute the contextualized data element to an EMR/EHR application that utilizes the label in the contextualized data element to perform a function that is related to the user writing on the form and wherein the contextualized data element is distributed to the EMR/EHR application via a publish/subscribe protocol in which the EMR/EHR application subscribes to a specific contextualized data element by identifying the label associated with the contextualized data element.

28. The system of claim 27, wherein the labels include taxonomic information.

* * * * *